US010993609B1

(12) United States Patent
Gilkey et al.

(10) Patent No.: US 10,993,609 B1
(45) Date of Patent: May 4, 2021

(54) IMAGING ELEMENT CLEANING DEVICE WITH IMAGING DEVICE FITMENT ADJUSTABILITY

(71) Applicant: ClearCam Inc., Austin, TX (US)

(72) Inventors: James Landon Gilkey, Dripping Springs, TX (US); Mitchell Ross Gilkey, Austin, TX (US)

(73) Assignee: ClearCam Inc., Austin, TX (US)

( * ) Notice: Subject to any disclaimer, the term of this patent is extended or adjusted under 35 U.S.C. 154(b) by 0 days.

(21) Appl. No.: 17/156,533

(22) Filed: Jan. 23, 2021

(51) Int. Cl.
*A61B 1/00* (2006.01)
*A61B 1/12* (2006.01)
*A61B 1/005* (2006.01)

(52) U.S. Cl.
CPC ............ *A61B 1/126* (2013.01); *A61B 1/0052* (2013.01); *A61B 1/00096* (2013.01)

(58) Field of Classification Search
None
See application file for complete search history.

(56) References Cited

U.S. PATENT DOCUMENTS

| 5,392,766 | A | 2/1995 | Masterson et al. |
| 5,518,502 | A | 5/1996 | Kaplan et al. |
| 5,695,448 | A * | 12/1997 | Kimura ................ A61B 1/0005 600/114 |
| 6,755,782 | B2 | 6/2004 | Ogawa |
| 6,923,759 | B2 | 8/2005 | Kasahara et al. |
| 7,543,314 | B2 | 6/2009 | Kadykowski |
| 7,959,561 | B2 * | 6/2011 | Akui ................ A61B 1/00087 600/157 |
| 8,690,764 | B2 | 4/2014 | Clark et al. |
| 8,979,738 | B2 | 3/2015 | Hsu et al. |
| 9,050,036 | B2 | 6/2015 | Poll et al. |
| 9,486,129 | B2 | 11/2016 | Rodriguez Sanjuan |
| 9,763,567 | B2 | 9/2017 | O'Prey et al. |

(Continued)

FOREIGN PATENT DOCUMENTS

| CN | 101883531 B | 7/2014 |
| EP | 0647425 A1 | 4/1995 |

(Continued)

OTHER PUBLICATIONS

International Search Authority, Notification of Transmittal of the International Search Report and Written Opinion of the International Search Authority, PCT/US2019/063369, 16 pages.

*Primary Examiner* — Timothy J Neal
(74) *Attorney, Agent, or Firm* — David O. Simmons; IVC Patent Agency

(57) ABSTRACT

Cleaning devices disclosed herein provide, for example, an effective and reliable approach for cleaning an exposed surface of an imaging element (e.g., a lens) of an imaging device (e.g., an endoscope). Cleaning devices disclosed herein enable an imaging element to be cleaned while located within a concealed operation site (e.g., an in-vivo surgical site). To enhance imaging device compatibility, cleaning devices disclosed herein have integral therewith a seating adjustor that allows a user to selectively adjust the position of an imaging device seated thereon. Cleaning devices disclosed herein are thus able to accommodate imaging devices that would otherwise be incompatible due to a distance between the imaging element of the imaging device and a position of a cleaning member of the cleaning device being either too big or too small.

26 Claims, 6 Drawing Sheets

(56) References Cited

U.S. PATENT DOCUMENTS

| | | | |
|---|---|---|---|
| 10,791,918 B1 | 10/2020 | Gilkey et al. | |
| 2009/0229067 A1 | 9/2009 | Becker et al. | |
| 2009/0250081 A1 | 10/2009 | Gordin et al. | |
| 2012/0101338 A1 | 4/2012 | O'Prey et al. | |
| 2014/0094650 A1 | 4/2014 | Schaning | |
| 2016/0128551 A1 | 5/2016 | Hsu et al. | |
| 2016/0143512 A1* | 5/2016 | Cheng .................. | A61B 1/015 600/123 |
| 2017/0332893 A1 | 11/2017 | Irion et al. | |
| 2017/0367571 A1 | 12/2017 | Nave | |

FOREIGN PATENT DOCUMENTS

| | | |
|---|---|---|
| JP | S5861723 A | 4/1983 |
| JP | H01204637 A | 8/1989 |
| JP | 04-362912 | 12/1992 |
| JP | H05103748 A | 4/1993 |
| JP | 2015031026 A | 2/2015 |
| JP | 5735908 B2 | 6/2015 |
| WO | 200912587 A2 | 10/2009 |
| WO | 2014034839 A1 | 3/2014 |
| WO | WO2017006684 | 12/2017 |
| WO | 2020112852 A1 | 4/2020 |

\* cited by examiner

IMAGING ELEMENT CLEANING DEVICE WITH IMAGING DEVICE FITMENT ADJUSTABILITY

FIELD OF THE DISCLOSURE

The disclosures made herein relate generally to cleaning of devices that utilize a remote imaging element for visualization of structures at a concealed site and, more particularly, to an imaging element cleaning device for cleaning an exposed surface of the imaging element while the exposed surface is located within a concealed site such as, for example, an in-vivo human or animal environment.

BACKGROUND

Surgical procedures utilizing in-vivo visualization of target surgical sites are well known as a form of a concealed operation site. Examples of these surgeries include, but are not limited to, endoscopic surgery, laparoscopic surgery, thoracoscopic surgery and the like. These surgical procedures utilize a surgical instrument having an integrated visualization device for providing in-vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope".

As shown in FIG. 1, an endoscope 1 used in laparoscopic surgical procedures is characterized as having a user interface portion 5 and an extension portion 10 connected at its proximate end 15 to the user interface portion 5. Examples of commercially-available endoscopes include, but are not limited to, endoscopes manufactured under brand names of Karl Storz, Linvatec, Olympus, Richard Wolf, Stryker and Intuitive Surgical. For simplicity, scope/camera apparatuses utilized with robotic surgical systems are referred to herein as endoscopes.

The extension portion 10 has an imaging element 20 such as a lens at its distal end portion 25. The imaging element 20 may have an exposed surface that is generally flush with or that defines an end face of the extension portion 10. The imaging element 20 is connected to an optical fiber or other image transmitting element that is internal to the endoscope. The optical fiber or other image transmitting element extends along the length of the extension portion 10 and terminates at an eyepiece 30 on the user interface portion 5. The eyepiece 30 enables the imaging element 30 to be connected to a visualization device (e.g., a camera connected to a visual display console) through which target surgical sites may be viewed by surgery personnel.

During a surgical procedure using the endoscope 1, the exposed surface of the imaging element 20 may become impaired due to one or more in-vivo scenarios. Examples of these scenarios include the exposed surface of the imaging element 20 becoming fogged with moisture within the surgical space, or the exposed surface of the imaging element 20 may be smeared by blood, fat or other bodily fluids or tissues (e.g. interstitial fluid, fat tissue or the like). To maintain required visualization of target surgical sites, it is desirable to clean the exposed surface of the imaging element 20 while the distal end portion of the extension portion 10 remains in the surgical site.

Various devices have been devised to clean an exposed surface of an imaging element of a device while the distal end portion of the device remains in a concealed operation site. In some implementations, such devices are configured as an article of manufacture that is selectively mountable on a commercially-available endoscope (i.e., a scope-mountable cleaning device). Examples of cleaning devices specifically adapted for use with endoscopes and the like are disclosed in the following United States patents and patent application publications, all of which are incorporated herein in their entirety by reference: US20160128551, US20090229067, U.S. Ser. No. 10/791,918, U.S. Pat. Nos. 9,050,036, 8,979,738, 7,959,561, 6,923,759, 6,755,782 and 5,518,502.

FIGS. 2 and 3 shows a cleaning device (i.e., cleaning device 50) configured for use with an endoscope, where such use is now discussed in reference to the endoscope 1 of FIG. 1. The cleaning device 50 has an elongated body 52 that is adapted to have the extension portion 10 of endoscope 1 inserted within a central passage 53 of the cleaning device 50 to a seated position S, as shown in FIG. 2. Cleaning functionality of the cleaning device 50 includes manipulation (e.g., rotation) of a control body 54 at a user interface body 56 of the cleaning device 50 to cause a corresponding movement of a cleaning member 58 at a distal end portion 60 of the elongated body 52. Such corresponding movement of the cleaning member 58 brings the cleaning member 58 into contact (or near contact) with the imaging element 20 of the endoscope 1 to remove contaminants therefrom.

Accordingly, placement of the cleaning member 58 relative to the imaging element 20 along a longitudinal centerline reference axis L1 of the elongated body 52 is important to achieving reliable and effective cleaning functionality. In its fully seated placement (i.e., seated position S), as shown in FIG. 2, a dimensionally predictable surface or feature of the endoscope 1 such as that of the user interface portion 5 (e.g., a handle and/or optic interface portion) abuts or engages a mating dimensionally predictable surface or feature of the cleaning device 50. This mating surface or feature of the cleaning device 50 (e.g., a surface or feature of a user interface body 55 thereof) serves as a reference structure of the cleaning device 50 to ensure consistent and predictable axial placement of the endoscope 1 on the cleaning device 50.

A cleaning device (e.g., the cleaning device 50) may accommodate a variety of models, brands and/or sizes of endoscopes relative to diametrical fitment of the extension portion 10 in the central passage 53 of the elongated body 52. However, conventional cleaning devices are configured for use with endoscopes having an extension portion (e.g., the extension portion 10 of the endoscope 1) of a specific known length (or length within a designated specification and/or tolerance) relative to the dimensionally predictable surface or feature thereof. Accordingly, a significant shortcoming arises when an otherwise compatible endoscope cannot be used with a given cleaning device solely because a length of the extension portion of the endoscope is nominally or marginally too short or too long relative to the length of the elongated body of the cleaning device when the endoscope is seated on the given cleaning device. In such situations, shown in FIG. 2, a distance D between the imaging element 20 of the endoscope 1 and a position of the cleaning member 58 of the cleaning device 50 is either too big or too small to allow use of the endoscope 1 with the cleaning device 50 i.e., either excessive contact of the imaging element 20 by the cleaning member 58 or insufficient contact of the imaging element 20 by the cleaning member 58.

Therefore, an effective, efficient, simple and reliable approach for enabling a cleaning device to accommodate endoscopes that would otherwise be incompatible with the cleaning device due to length differences between the extension portion of the endoscope and cleaning member position when the endoscope is seated on the cleaning device would be advantageous, desirable and useful.

SUMMARY OF THE DISCLOSURE

Embodiments of the disclosures made herein are directed to increasing compatibility between a given cleaning device and endoscopes (e.g., commercially-available endoscopes). More specifically, a cleaning device in accordance with the disclosures made herein includes a seating adjustor that allows a user to selectively adjust the position of an endoscope seated thereon. Such a cleaning device is thus able to accommodate endoscopes that would otherwise be incompatible due to dimensional considerations of the endoscope and cleaning device resulting in a distance between the imaging element of the endoscope and a position of the cleaning member of the cleaning device being either too big or too small to allow use of the endoscope with the cleaning device. The dimensional considerations may arise from differences in specified dimensions (e.g., an endoscope's extension portion length). In this manner, cleaning devices in accordance with the disclosures made herein advantageously may extend their utility across a plurality of different models, brands and/or sizes of endoscopes.

In one or more embodiments of the disclosures made herein, an endoscope cleaning device adapted for having an endoscope engaged therewith in a seated position relative thereto comprises a main body (e.g., a chassis or user interface body) and a positioning member. The main body is adapted to enable the endoscope to be at least partially engaged with the endoscope cleaning device through the main body—e.g., at least a portion of the endoscope is coupled to or mounted on the main body. The positioning member is coupled to the main body to be selectively moved to and retained in any one of a plurality of adjustment positions relative to the main body. The positioning member includes an endoscope engaging portion that engages a corresponding portion of the endoscope while the endoscope is engaged with the endoscope cleaning device such that the positioning member being retained in a selected one of the adjustment positions and being engaged the corresponding portion of the endoscope at least partially defines the seated position.

In one or more embodiments of the disclosures made herein, an endoscope cleaning device comprises a chassis and a seating adjustor. The chassis is adapted for having an endoscope engaged therewith in a seated position relative to the chassis. The seating adjustor is integral with the chassis. The seating adjustor includes an adjuster body and a positioning member. The adjuster body is attached to the chassis for being selectively moved between a plurality of adjustment positions relative to the chassis. The positioning member is interlockedly attached to the adjuster body whereby the adjuster body being in a selected one of the plurality of adjustment positions causes the positioning member to be in a corresponding seating position relative to the adjustor body. The positioning member has an endoscope engaging portion engaged by a corresponding portion of the endoscope while the endoscope is engaged with the chassis such that the corresponding seating position of the positioning member relative to the chassis at least partially defines the seated position.

In one or more embodiments of the disclosures made herein, an endoscope cleaning device comprises a chassis and a seating adjustor integral with the chassis. The chassis is adapted for having an endoscope engaged therewith in a seated position relative to the chassis. The adjustor includes an adjuster body rotatably mounted on the chassis and a positioning member threadedly engaged at a first end portion thereof with a mating portion of the adjuster body whereby a rotational position of the adjustor body relative to the chassis defines a corresponding seating position of the positioning member relative to the chassis. The positioning member has an endoscope engaging portion at a second end portion thereof that engages a corresponding portion of the endoscope while the endoscope is engaged with the chassis such that the corresponding seating position of the positioning member relative to the chassis at least partially defines the seated position.

In one or more embodiments, the main body includes a passage adapted for having an extension portion of the endoscope received therein.

In one or more embodiments, the positioning member is movably mounted on the main body to be moved axially along a reference axis extending parallel to a centerline longitudinal axis of the passage.

In one or more embodiments, the seating adjustor is mounted on the user interface body.

In one or more embodiments, the positioning member is coupled to the main body through an adjustor body mounted on the main body.

In one or more embodiments, the positioning member includes an elongated portion slidably mounted on the main body to be axially translated along a centerline longitudinal axis of the elongated portion.

In one or more embodiments, seating positions of the positioning member each corresponding to a respective one of the adjustment positions of the adjustor body lay along the centerline longitudinal axis of the elongated portion.

In one or more embodiments, the positioning member is interlockedly (e.g., threadedly) attached to the adjustor body such that each rotational position of the adjustor body relative to the main body defines a corresponding adjustment position of the positioning member.

In one or more embodiments, the main body includes a user interface body and an elongated body attached thereto.

In one or more embodiments, the elongated body has a central passage accessible through an opening in the user interface body thereby enabling an extension portion of the endoscope to be slidably inserted into the central passage through the opening.

In one or more embodiments, the main body comprises a light port receptacle in which a light port of the endoscope resides while the endoscope is engaged with the endoscope cleaning device.

In one or more embodiments, the light port receptacle is integral with the user interface body.

In one or more embodiments, the endoscope engaging portion of the positioning member is located within a light port receiving space of the light port receptacle to engage the light port of the endoscope while the endoscope is engaged with the endoscope cleaning device.

These and other objects, embodiments, advantages and/or distinctions of the present invention will become readily apparent upon further review of the following specification, associated drawings and appended claims.

DETAILED DESCRIPTION

Figure 1:
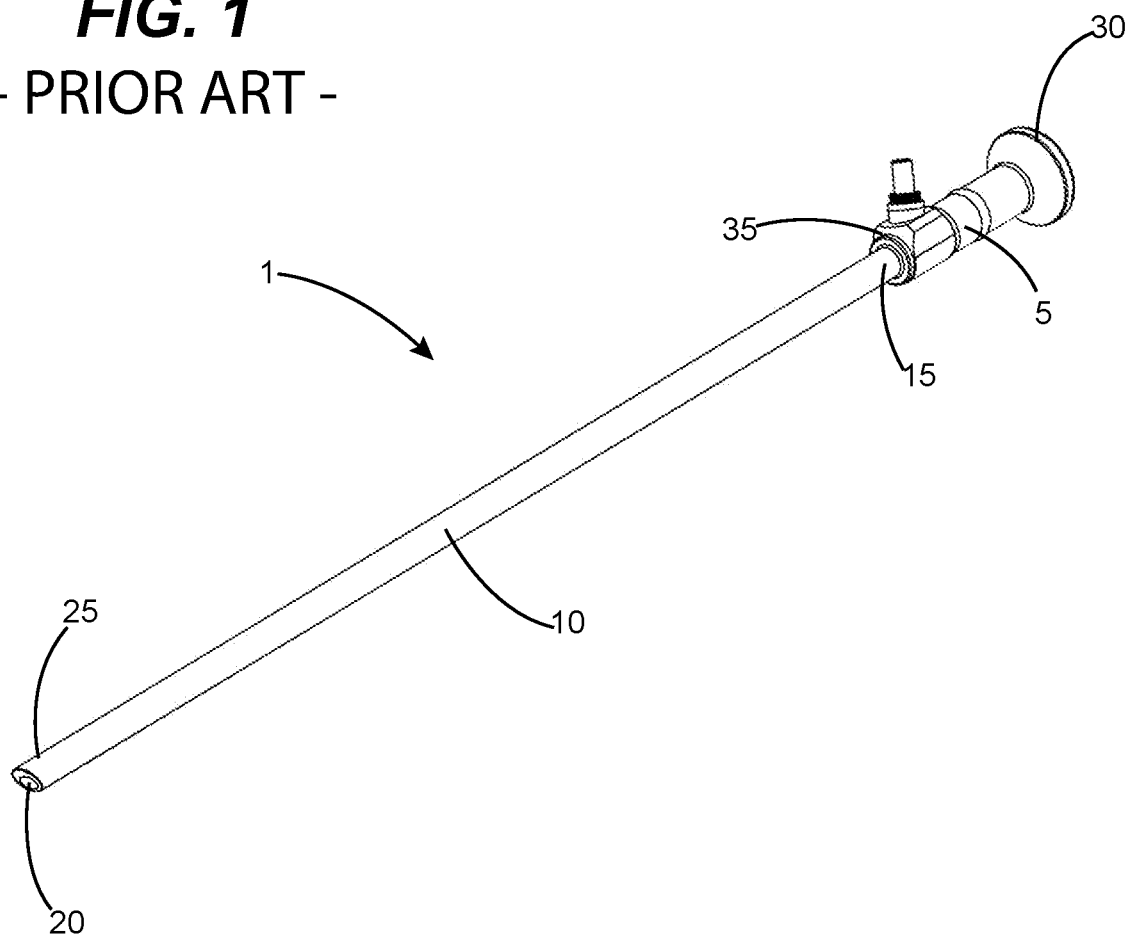
FIG. 1 is a perspective view showing a prior art endoscope.
Figure 2:
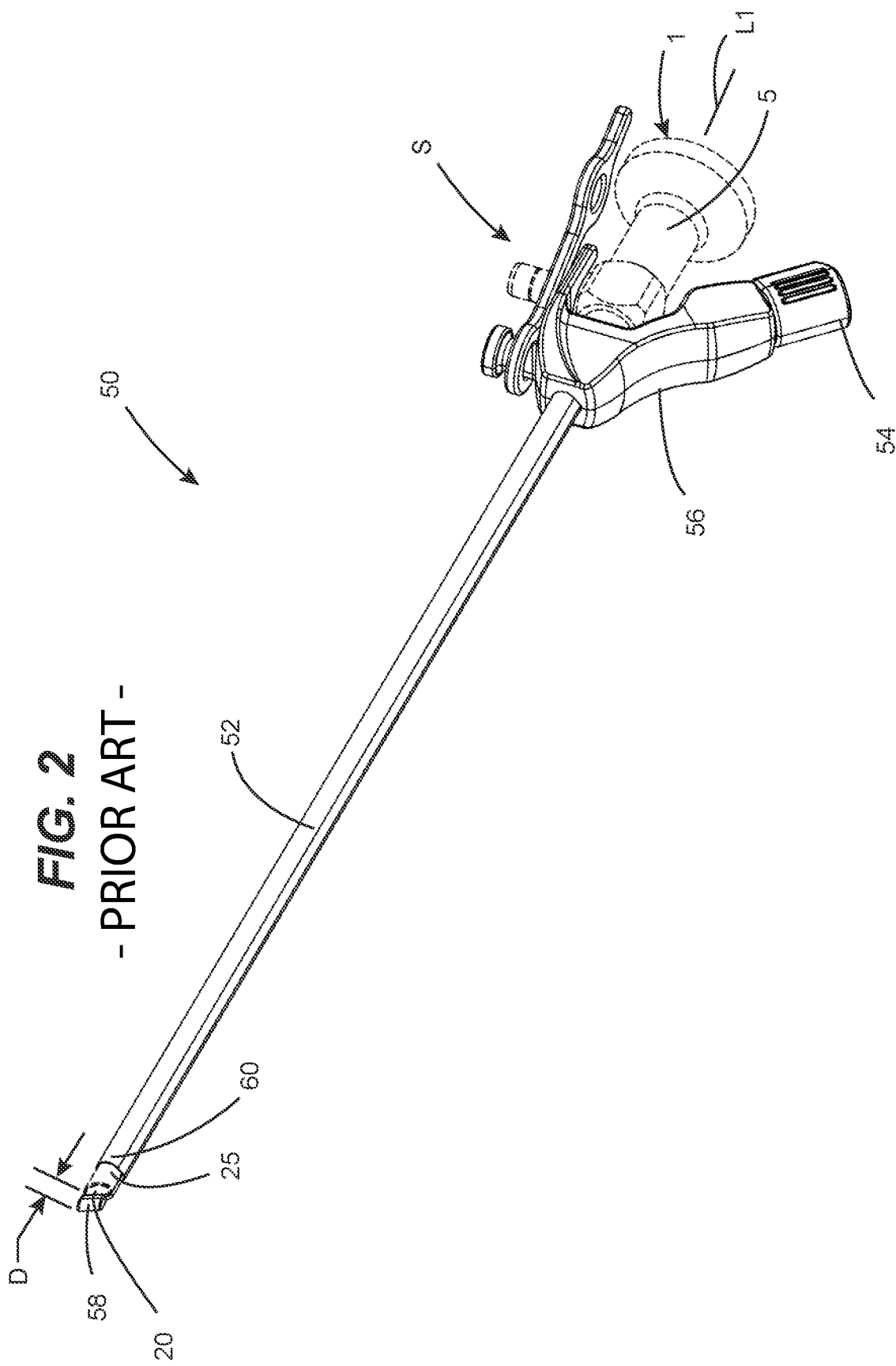
FIG. 2 is a first perspective view showing a prior art cleaning device in accordance with a first embodiment of the disclosures made herein.
Figure 3:
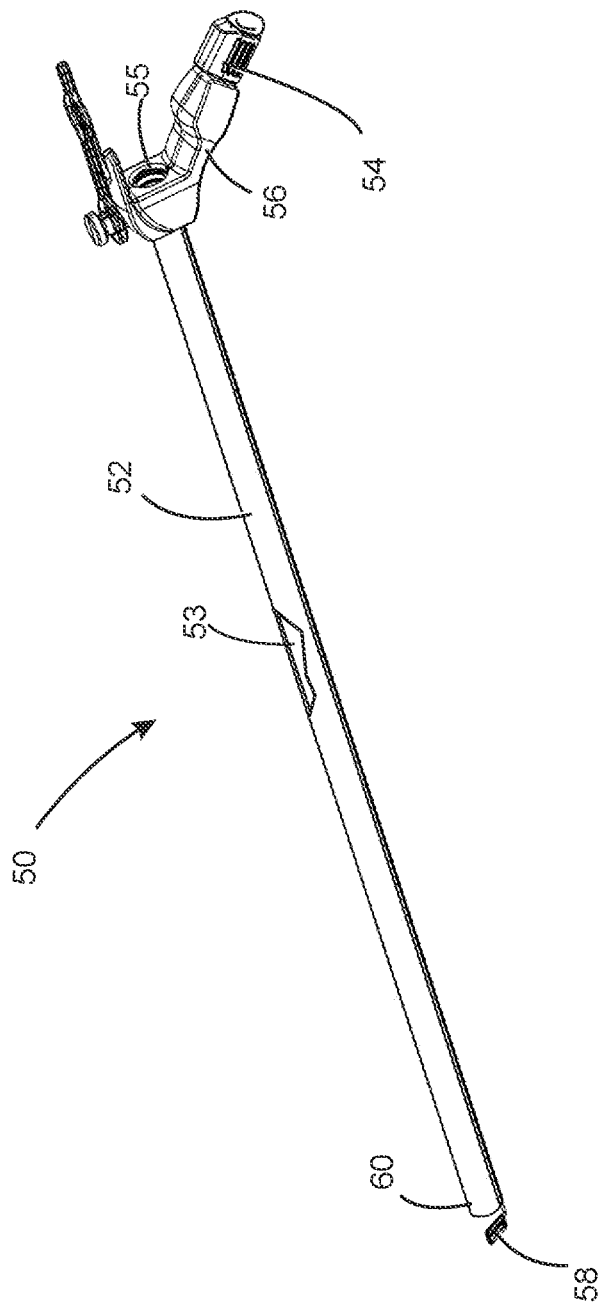
FIG. 3 is a second perspective view showing the prior art cleaning device of FIG. 2.

FIGS. 4-8 illustrate various aspects of an endoscope cleaning device configured in accordance with one or more embodiments of the disclosures made herein, which is designated as cleaning device 100. Cleaning device 100 is preferably, but not necessarily, configured to be used with commercially-available endoscopes, such as endoscope 1 of FIG. 1. In some embodiments, the cleaning device 100 is preferably, but not necessarily, configured to be used with endoscopes manufactured under brand names of Karl Storz, Linvatec, Olympus, Richard Wolf, Stryker and Intuitive Surgical.

The cleaning device 100 includes a seating adjustor 101 that enables a user to selectively adjust a seated position S of an endoscope (e.g., the endoscope 1) attached to the cleaning device 100. As discussed below in greater detail, the cleaning device 100 is thus able to accommodate one or more endoscopes that would otherwise be incompatible with the cleaning device 100 due to certain dimensional considerations of such one or more endoscopes. Accordingly, the cleaning device 100 advantageously may extend its utility across a plurality of different models, brands and/or sizes of endoscopes.

Figure 4:
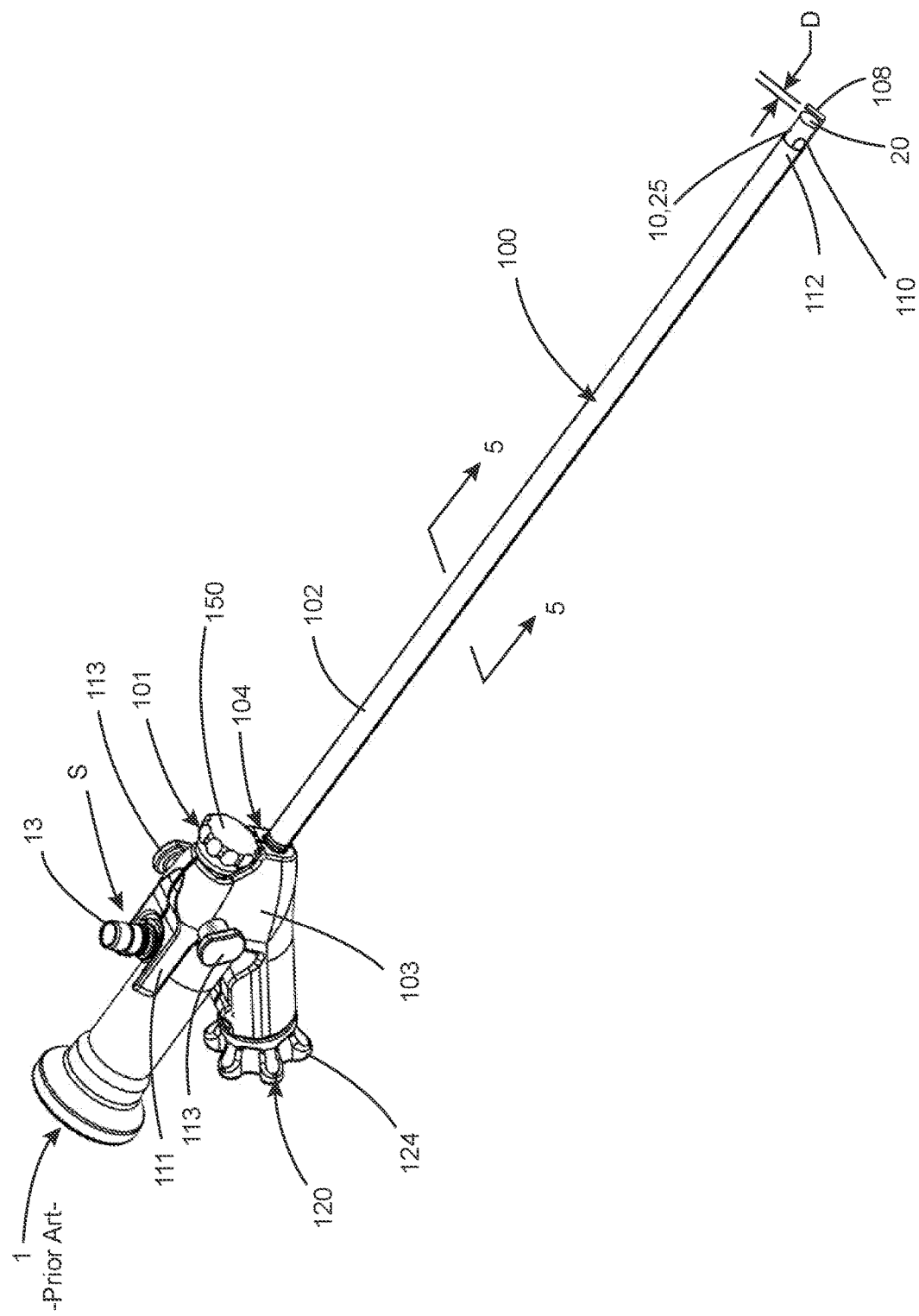
FIG. 4 is perspective view of an endoscope cleaning device in accordance with one or more embodiments of the disclosures made herein.

The cleaning device 100 includes an elongated body 102 and a user interface body 103, which jointly define a chassis 104. The chassis 104 serves as the platform on which an endoscope may be mounted in a predictable seated position (i.e., the seated position S, as shown in FIG. 4). In one or more embodiments, the user interface body 103 or the chassis 104 may be a main body of the cleaning device 100. The elongated body 102 may be a tube having a central passage 106 with a round or generally round cross-sectional shape. The central passage 106 may be accessible through a mating opening 106' (or other form of passage) within the user interface body 103 thereby enabling the extension portion 10 of the endoscope 1 to be inserted into the central passage 106 through the opening 106'.

The central passage 106 has a size and profile that is adapted to have the extension portion 10 of the endoscope 1 engaged therein by inserting the extension portion into the central passage 106 and sliding the extension portion 10 along the length of the elongated body 102 until the endoscope 1 is in the seated position S on the chassis 104. Alternatively, the elongated member 102 may be a non-tubular structure such as a skeletal-type structure that engages the extension portion 10 of the endoscope 1—e.g., at discrete spaced-apart locations thereof. It is disclosed herein that the chassis 104 may be that of a robot that provides robot-assisted surgery or may be adapted to operatively interface with a mating mounting portion of such a robot. For example, the elongated body 102 and/or the user interface body 103 may be that of an arm or other structure of the robot or adapted to operatively interface with an instrument mounting portion of the arm of the robot.

The chassis 104 may include a plurality of structural elements that provide for the known and predictable position of the endoscope 1 when mounted in the seated position S on the chassis 104. One of these structural elements is the effective inside diameter (e.g., for ribbed or textured interior surface) or the actual inside diameter (e.g., a smooth interior wall) of the elongated body 102 in relation to an outside diameter of the extension portion 10 of the endoscope 1. It is preferable to maintain a close fit between the outside wall of elongated body 102 and the mating exterior surface of the extension portion 10 so as to provide for a fluid-resistant interface between the elongated body 102 and the extension portion 10 and to limit off-axis pitch between a longitudinal axis of the elongated body 102 and a longitudinal axis of the extension portion 10. When the endoscope 1 is fully compatible with the cleaning device 100, another one of these structural elements is a seating surface 107 (shown in FIG. 7) on the user interface body 103. The seating surface 107 may be a reference surface of the cleaning apparatus 100 that engages a mating reference surface 35 (shown in FIG. 1) of the endoscope 1. Engagement of the seating surface 107 with the mating reference surface 35 of the endoscope 1 serves to define a predictable seated position of the endoscope 1 on the chassis 104. However, as discussed below in greater detail, the seating adjustor 101 and a respective mating portion of the endoscope 1 provide such predictable seated position of the endoscope 1 on the chassis 104 when the endoscope 1 is not fully compatible with the cleaning device 100.

To provide for securement between and/or rotational clocking of the endoscope 1 and the cleaning device 100, the user interface body 103 may include a light port receptacle 111 and securement bodies 113. The light port receptacle 111 has a light port receiving space 115 in which a light port 13 of the endoscope 1 is received (e.g., constrained by engagement of mating surfaces) while the endoscope 1 is engaged with the cleaning device 100. A retention structure (e.g., an elastic strap, band of the like) may be engaged with one or both of the securement bodies 113 to secure the endoscope 1 and the cleaning device 100 in fixed, seated engagement.

The cleaning apparatus 100 may include a cleaning member 108 adjacent to an opening 110 in a distal end portion 112 of the elongated body 102. The cleaning member 108 functions to clean contaminants and debris from a surface of the imaging element 20 of the endoscope 1 when brought into contact with the imaging element 20. To this end, the cleaning device 100 may include a cleaning member controller 120 (i.e., a cleaning member control mechanism) that is coupled to the cleaning member 108 to enable the cleaning member 108 to be selectively brought into contact with the imaging element 20 of the endoscope 1. In one or more embodiments, the cleaning member 108 may be coupled to the cleaning member controller 120 through a coupling element 116, where the cleaning member 108 is attached to a distal end portion of the coupling element 116 and the cleaning member controller 120 is attached to a proximate end portion of the coupling element 116. Through manipulation of a user interface portion of the cleaning member controller 120 (e.g., rotation of a control body 124), the cleaning member 108 may be selectively rotated into and away from contact with the imaging element 20 for removing (e.g., wiping) contaminants from the surface of the imaging element 20.

Figure 5:
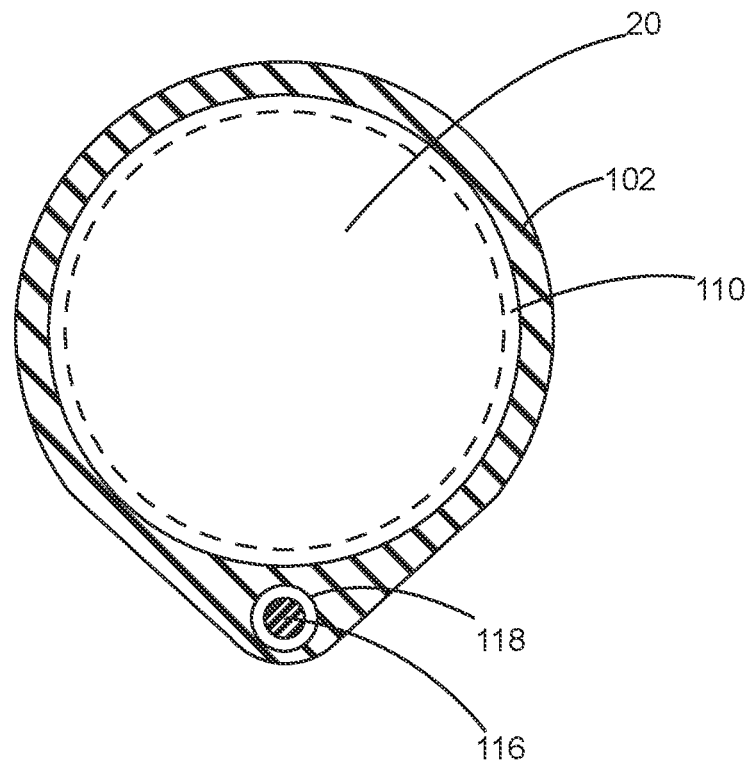
FIG. 5 is a cross-sectional view taken along the line 5-5 in FIG. 4.

As best shown in FIG. 5, the coupling element 116 may extend through a channel 118 within the elongated body 102. Preferably, the channel 118 and the central passage 106 extend substantially parallel to each other within the elongated body 102. In some embodiments, the coupling element 116 may be an elongated small diameter structure that offers at least a limited degree of bendability in combination with high torsional rigidity. In other embodiments, the coupling element 116 is characterized by an elongated small diameter structure that offers a given amount of torsional compliance. Based on these characterizing attributes, examples of coupling element 116 include, but are not limited to, solid metallic wire, spiraled metal wire, a polymeric filament(s), a composite filament(s) or the like.

In one or more other embodiments, the cleaning member 108 may be replaced with a non-contact cleaning structure. For example, the non-contact cleaning structure may be a jet, nozzle or the like through which a gaseous, liquid or other type of flowable medium is delivered to/directed upon a surface of the imaging element 20 of the endoscope 1. Examples of cleaning devices incorporating a non-contact cleaning structure are disclosed in the following patents and patent application publications: US20140371763, US20100198014, US20080200765, U.S. Ser. No. 10/398, 292, U.S. Pat. No. 9,050,036, EP0497347A2, all of which are incorporated herein in their entirety by reference.

Often, endoscopes of different models, brands and/or sizes often have a respective extension portion that are each of a common or suitably nominal outside diameter, thereby enabling such extension portions to all be operably received within a central passage of an elongated body of a given cleaning device (e.g., the cleaning device 100). However, even with such endoscopes having such diametrical compatibility with respect to the elongated body of the given endoscope, one or more of such endoscopes may have one or more other dimensional considerations (e.g., extension member length, seating surface size/shape, light port placement, etc.) that result in an incompatibility with the given cleaning device whereby cleaning functionality is adversely affected or entirely precluded. This incompatibility is known to arise from such one or more other dimensional considerations of a particular endoscope causing a distance between the imaging element of the particular endoscope and a position of the cleaning member of the cleaning device (i.e., the distance D shown in FIG. 4) being either too big or too small to allow use of the particular endoscope with the cleaning device. In some embodiments, this distance may cause the cleaning member to be brought into contact with the exposed surface of the imaging element under a suitable degree of load to provide intended cleaning functionality of the exposed surface of the imaging element (i.e., to wipe contaminants away) when the cleaning member is moved across the imaging element. In some other embodiments, this distance may be such that the cleaning member may be spaced away from the imaging element by a nominal amount to knock beads of liquid, pieces of solid material or other contaminant away from the exposed surface of the imaging element (i.e., without touching such exposed surface) when the cleaning member is moved over the imaging element— e.g., less than one-tenth of an inch, less than an average diameter of a typical bead of liquid on the imaging element, etc.

Advantageously, cleaning devices configured in accordance with the disclosures made herein each include a seating adjustor. The underlying functionality of the seating adjustor is to enable adjustment of a seated position of an endoscope engaged with the chassis of such a cleaning device. Such adjustment is a "gross" adjustment to achieve a distance between the imaging element of the particular endoscope and a position of the cleaning member of the cleaning device suitable for enabling intended imaging element cleaning functionality (i.e., the distance D shown in FIG. 4). In this regard, adjustability of the seated position enables such a cleaning device to accommodate one or more endoscopes that would otherwise be incompatible with the cleaning device.

The adjuster body 150 may be rotatably (i.e., movably) mounted on the user interface body 103 with the positioning member 152 interlockedly engaged therewith. For example, as shown, a first end portion 154 of the positioning member 152 thereof may have threads that engage threads of a mating portion of the adjuster body 150 (e.g., a mounting portion thereof) such that the adjuster body 150 and the positioning member 152 are threadedly engaged. In this manner, movement (e.g., rotation) of the adjuster body 150 to a selected one of a plurality of adjustment positions (e.g., a selected rotational position) relative to the chassis 140 defines a corresponding axial position (i.e., seating position) of the positioning member 152 relative to the chassis 104. Thus, engagement of the endoscope 1 with the chassis 104 causes the positioning member 152 to become engaged with a mating portion of the endoscope 1 (e.g., a light port thereof) whereby such the adjusted position of the adjustment body 150 defines or partially defines the seated position S of the endoscope 1 relative to the chassis 104.

Figure 8:
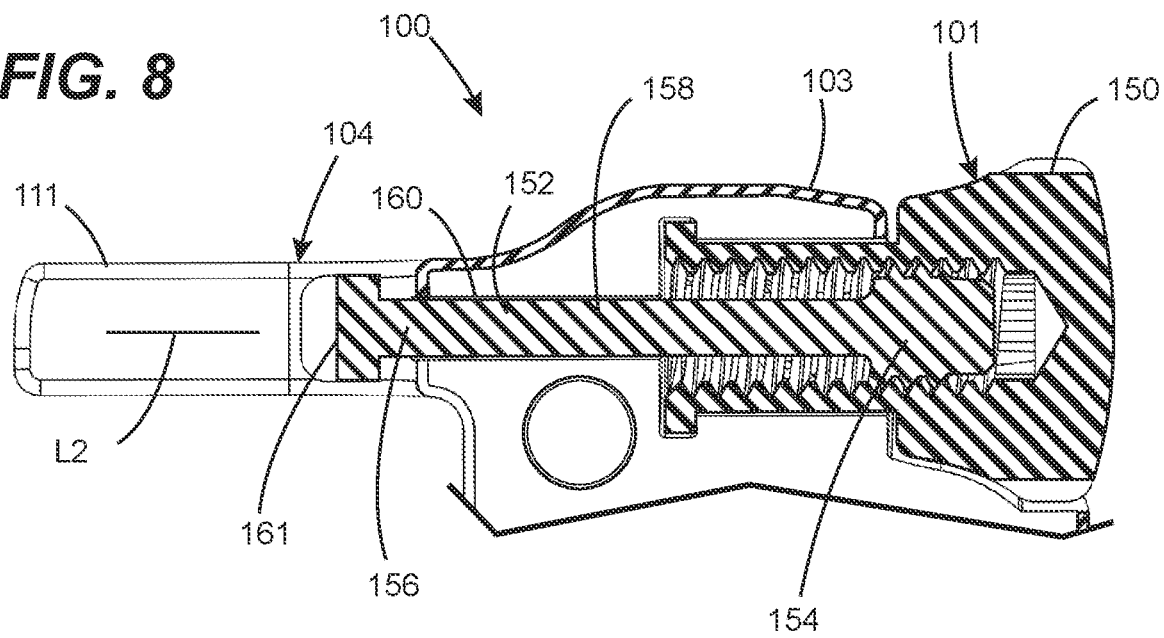
FIG. 8 is a cross-sectional view taken along the line 8-8 in FIG. 6.
Figure 6:
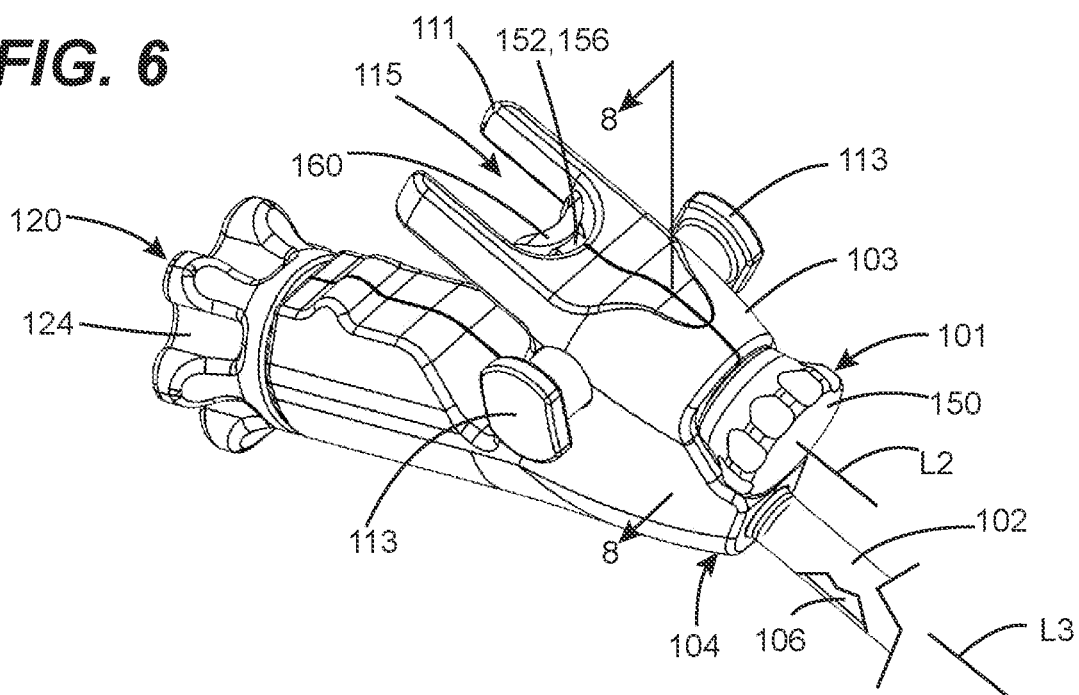
FIG. 6 is a first enlarged fragmentary perspective view of the endoscope cleaning device shown in FIG. 4.
Figure 7:
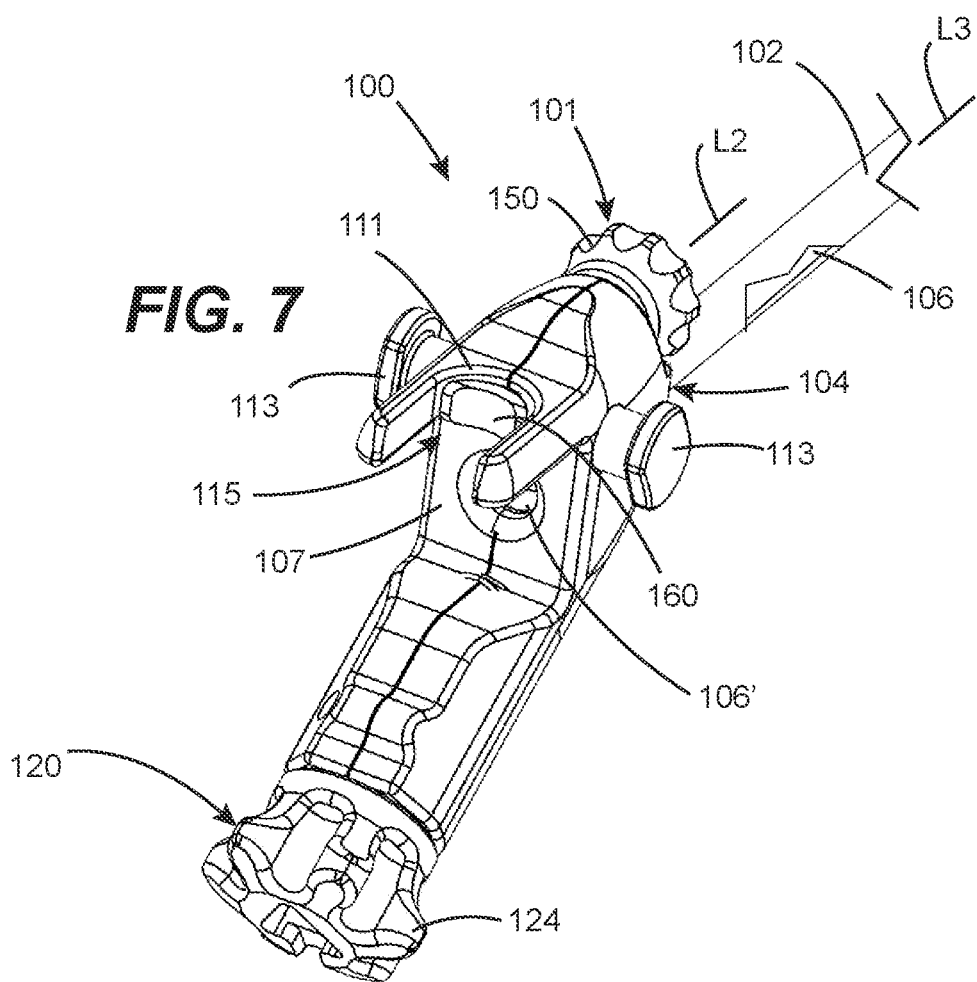
FIG. 7 is a second enlarged fragmentary perspective view of the endoscope cleaning device shown in FIG. 4.

Referring to FIGS. 6-8, the seating adjustor 101 of the cleaning device 100 (i.e., a cleaning device configured in accordance with the disclosures made herein) is coupled to (e.g., integral with or attached to) the chassis 104. For example, the seating adjustor 101 may be a plurality of components each mounted on/attached to the chassis 104 (as shown), a unitary component assembly mounted on the chassis 104 or the like. In one or more embodiments, as shown, the seating adjustor 101 includes an adjuster body 150 and a positioning member 152.

A distal portion (e.g., a second end portion 156) of the positioning member 152 may be translatably mounted on the user interface body 103 to enable sliding of the positioning member 152 along its longitudinal centerline axis L2 while inhibiting unrestricted rotation about the longitudinal centerline axis L2. Thus, a plurality of seating positions of the positioning member 152 each corresponding to a respective one of the adjustment positions of the adjuster body 150 lay along the longitudinal centerline axis L2 of the positioning member 152. In one example, an elongated portion 158 of the positioning member 152 and a mating passage 160 of the user interface body 103 may be jointly configured, such as through mating cross-sectional shaped, to inhibit rotation about the longitudinal centerline axis L2. In another example, the second end portion 156 of the positioning member 152 may include an engagement member 161 that serves to inhibit unrestricted rotation about the longitudinal centerline axis L2 by engaging one or more mating surfaces of the chassis (e.g., surfaces of the light port 111). The engagement member 161 may have a surface with a contour matching or mating that of an engaged portion of the endoscope 1 (e.g., s saddle-shaped contour that matingly engages an exterior portion of the light port 13).

Threaded engagement of the adjuster body 150 and the positioning member 152 is one example of an interlocked engagement enabling the positioning member 152 to be selectively moved to and retained in a plurality of different seating positions. In view of the disclosures made herein, a person of ordinary skill in the art will recognize other approaches for coupling a positioning member of an adjustor body for enabling the positioning member to be selectively moved to and retained in a plurality of different seating positions. In one example, a seating adjustor may be configured generally as the seating adjuster 101 shown in FIGS. 6-8, except with the adjustor body having a series of stepped surfaces that engage a mating surfaces of the positioning member whereby rotation of the adjustor body displaces the positioning member by a distance defined by a respective one of the stepped surfaces. In another example, the adjustor body of the previous example may be replaced by a retention member (e.g., one or more clips) that jointly engage the positioning member and the chassis of the cleaning device to retain the positioning member in a selected seated position. In still another example, the positioning member may be in the form of a body having a plurality of different length or shape endoscope engaging members extending therefrom, where each of the endoscope engaging members is movable to a position for engagement by an endoscope through rotation of the body about the longitudinal centerline axis L2 (e.g., via manipulation of an adjustor body). In yet example, the positioning member may be in the form of a body having a plurality of different length or shape endoscope engaging members extending therefrom, where each of the endoscope engaging members is movable to a position for engagement by an endoscope through rotation of the body about an axis of rotation extending perpendicular to the longitudinal centerline axis L2 (e.g., via manipulation of an adjustor body). Preferably, the longitudinal centerline axis L2 of the positioning member 152 extends parallel with a longitudinal centerline axis L3 of the central passage 106.

Beneficially, adjustability afforded by a seating adjustor of a cleaning device in accordance with the disclosures made herein (e.g., the seating adjuster 101 disclosed in reference to FIGS. 4 and 6-8) may increase the number of endoscopes compatible with a given cleaning device. The range of adjustment of the seating adjustor (i.e., overall length of adjustment in adjustment positions) allows such given cleaning device to adjust for endoscopes whose extension portion would otherwise be in an incompatible position relative to the cleaning member. For example, without the utility of the seating adjustor and depending on the specific physical construction of a particular endoscope, the imaging element of the particular endoscope may extend too far toward/past the cleaning member or not close enough to the cleaning member. Additionally, in the case of the seating adjustor offering a suitable resolution of adjustment (e.g., relatively fine-tune adjustment), the seating adjustor may also be utilized for adjusting a level of contact force between an imaging element of the endoscope (e.g., a lens) and the cleaning member.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An endoscope cleaning device adapted for having an endoscope engaged therewith in a seated position relative thereto, comprising:
   a main body at least partially through which the endoscope is engaged with the endoscope cleaning device; and
   a positioning member coupled to the main body to be selectively moved to and retained in any one of a plurality of adjustment positions relative to the main body and wherein the positioning member includes an endoscope engaging portion that engages a corresponding portion of the endoscope while the endoscope is engaged with the endoscope cleaning device such that the positioning member being retained in a selected one of the adjustment positions and being engaged with the corresponding portion of the endoscope at least partially defines the seated position, wherein the positioning member is coupled to the main body through an adjustor body that is rotatably mounted on the main body and wherein the positioning member is threadedly attached to the adjustor body such that each rotational position of the adjustor body relative to the main body defines a corresponding adjustment position of the positioning member.

2. The endoscope cleaning device of claim 1 wherein:
   the main body includes a passage adapted for having an extension portion of the endoscope received therein; and
   the positioning member is movably mounted on the main body to be moved axially along a reference axis extending parallel to a centerline longitudinal axis of the passage.

3. The endoscope cleaning device of claim 1 wherein the positioning member includes an elongated portion slidably mounted on the main body to be axially translated along a centerline longitudinal axis of the elongated portion.

4. The endoscope cleaning device of claim 3 wherein seating positions of the positioning member each corresponding to a respective one of the adjustment positions lay along the centerline longitudinal axis of the elongated portion.

5. The endoscope cleaning device of claim 4 wherein:
   the main body includes a passage adapted for having an extension portion of the endoscope received therein; and
   the positioning member is movably mounted on the main body to be moved axially along a reference axis extending parallel to a centerline longitudinal axis of the passage.

6. The endoscope cleaning device of claim 1 wherein:
   the main body comprises a light port receptacle in which a light port of the endoscope resides while the endoscope is engaged with the endoscope cleaning device; and
   the endoscope engaging portion of the positioning member is located within a light port receiving space of the light port receptacle to engage the light port of the endoscope while the endoscope is engaged with the endoscope cleaning device to thereby define the seated position thereof.

7. The endoscope cleaning device of claim 6 wherein:
   the main body includes a passage adapted for having an extension portion of the endoscope received therein; and the positioning member is movably mounted on the main body to be moved axially along a reference axis extending parallel to a centerline longitudinal axis of the passage.

8. An endoscope cleaning device, comprising:
a chassis adapted for having an endoscope engaged therewith in a seated position relative thereto; and
a seating adjustor integral with the chassis, wherein the seating adjustor includes an adjuster body and a positioning member, wherein the adjuster body is attached to the chassis for being selectively moved between a plurality of adjustment positions relative to the chassis, wherein the positioning member is interlockedly attached to the adjuster body whereby the adjuster body being in a selected one of the plurality of adjustment positions causes the positioning member to be in a corresponding seating position relative to the adjustor body and wherein the positioning member has an endoscope engaging portion engaged by a corresponding portion of the endoscope while the endoscope is engaged with the chassis such that the corresponding seating position of the positioning member relative to the chassis at least partially defines the seated position, wherein the adjustor body is rotatably attached to the chassis and wherein the positioning member is movably attached to the chassis and wherein the positioning member being interlockedly attached to the adjuster body includes the positioning member being threadedly attached to the adjuster body such that each adjustment position of the adjustor body is a rotational position thereof.

9. The endoscope cleaning device of claim 8 wherein:
the chassis includes a channel adapted for having an extension portion of the endoscope slidably received therein; and
the positioning member is movably mounted on the chassis to be moved axially along a reference axis extending parallel to a centerline longitudinal axis of the channel.

10. The endoscope cleaning device of claim 9 wherein:
the chassis includes a user interface body and an elongated body attached thereto;
the elongated body has a central passage accessible through an opening in the user interface body thereby enabling an extension portion of the endoscope to be slidably inserted into the central passage through the opening;
the central passage and the opening jointly define the channel.

11. The endoscope cleaning device of claim 8 wherein:
the chassis includes a user interface body and an elongated body attached thereto;
the elongated body has a central passage accessible through an opening in the user interface body thereby enabling an extension portion of the endoscope to be slidably inserted into the central passage through the opening; and
the seating adjustor is mounted on the user interface body.

12. The endoscope cleaning device of claim 8 wherein the chassis comprises a light port receptacle in which a light port of the endoscope resides while the endoscope is engaged with the chassis in the seated position.

13. The endoscope cleaning device of claim 12 wherein the endoscope engaging portion of the positioning member is located within a light port receiving space of the light port receptacle to engage the light port of the endoscope while the endoscope is engaged with the chassis to thereby define the seated position thereof.

14. The endoscope cleaning device of claim 13 wherein:
the chassis includes a user interface body and an elongated body attached thereto;
the elongated body has a central passage accessible through an opening in the user interface body thereby enabling an extension portion of the endoscope to be slidably inserted into the central passage through the opening;
the light port receptacle is integral with the user interface body; and
the seating adjustor is mounted on the user interface body.

15. The endoscope cleaning device of claim 13 wherein:
the chassis includes a channel adapted for having an extension portion of the endoscope inserted therein; and
a position of the endoscope engaging portion of the positioning member within the light port receiving space of the light port receptacle defines a maximum insertion depth of the extension portion of the endoscope into the channel while the endoscope is engaged with the chassis.

16. The endoscope cleaning device of claim 8 wherein:
the chassis includes a user interface body and an elongated body attached thereto;
the elongated body has a central passage accessible through an opening in the user interface body thereby enabling an extension portion of the endoscope to be slidably inserted into the central passage through the opening;
the central passage and the opening jointly define the channel.

17. An endoscope cleaning device, comprising:
a chassis adapted for having an endoscope engaged therewith in a seated position relative thereto; and
a seating adjustor integral with the chassis, wherein the seating adjustor includes an adjuster body rotatably mounted on the chassis and a positioning member threadedly engaged at a first end portion thereof with a mating portion of the adjuster body whereby a rotational position of the adjustor body relative to the chassis defines a corresponding seating position of the positioning member relative to the chassis and wherein the positioning member has an endoscope engaging portion at a second end portion thereof that engages a corresponding portion of the endoscope while the endoscope is engaged with the chassis such that the corresponding seating position of the positioning member relative to the chassis at least partially defines the seated position.

18. The endoscope cleaning device of claim 17 wherein:
the positioning member includes an elongated portion between the first and second end portions of the positioning member; and
the elongated portion is slidably mounted on the chassis.

19. The endoscope cleaning device of claim 17 wherein:
the chassis includes a channel adapted for having an extension portion of the endoscope slidably received therein; and
the positioning member is movably mounted on the chassis to be moved axially along a reference axis extending parallel to a centerline longitudinal axis of the channel.

20. The endoscope cleaning device of claim 19 wherein:
the chassis includes a user interface body and an elongated body attached thereto;
the elongated body has a central passage accessible through an opening in the user interface body thereby enabling an extension portion of the endoscope to be slidably inserted into the central passage through the opening;
the central passage and the opening jointly define the channel;
the adjustor body is rotatably attached to the user interface body; and
the positioning member is slidably attached to the user interface body.

21. The endoscope cleaning device of claim 17 wherein:
the chassis includes a user interface body and an elongated body attached thereto;
the elongated body has a central passage accessible through an opening in the user interface body thereby enabling an extension portion of the endoscope to be slidably inserted into the central passage through the opening; and
the seating adjustor is integral with the user interface body.

22. The endoscope cleaning device of claim 17 wherein:
the chassis comprises a light port receptacle in which a light port of the endoscope resides while the endoscope is engaged with the chassis in the seated position; and
the endoscope engaging portion of the positioning member engages the light port of the endoscope while the endoscope is engaged with the chassis to define the seated position of the endoscope in the seated position.

23. The endoscope cleaning device of claim 22 wherein the endoscope engaging portion of the positioning member is located within a light port receiving space of the light port receptacle to engage the light port of the endoscope while the endoscope is engaged with the chassis to thereby define the seated position thereof.

24. The endoscope cleaning device of claim 23 wherein:
the chassis includes a user interface body and an elongated body attached thereto;
the elongated body has a central passage accessible through an opening in the user interface body thereby enabling an extension portion of the endoscope to be slidably inserted into the central passage through the opening;
the light port receptacle is integral with the user interface body; and
the seating adjustor is mounted on the user interface body.

25. The endoscope cleaning device of claim 23 wherein:
the positioning member includes an elongated portion between the first and second end portion of the positioning member; and
the elongated portion is slidably mounted on the chassis.

26. The endoscope cleaning device of claim 23 wherein:
the chassis includes a channel adapted for having an extension portion of the endoscope slidably received therein; and
the positioning member is movably mounted on the chassis to be moved axially along a reference axis extending parallel to a centerline longitudinal axis of the channel.

* * * * *